United States Patent
Mongiorgi et al.

(10) Patent No.: US 8,075,680 B2
(45) Date of Patent: Dec. 13, 2011

(54) DENTAL CEMENT

(75) Inventors: Romano Mongiorgi, Marzabotto (IT); Maria Giovanna Gandolfi, Bologna (IT); Carlo Prati, Bologna (IT)

(73) Assignee: Alma Mater Studiorum-Universitá Di Bologna, Bologna (IT)

( * ) Notice: Subject to any disclaimer, the term of this patent is extended or adjusted under 35 U.S.C. 154(b) by 94 days.

(21) Appl. No.: 12/525,767

(22) PCT Filed: Feb. 8, 2008

(86) PCT No.: PCT/EP2008/051583
§ 371 (c)(1),
(2), (4) Date: Sep. 25, 2009

(87) PCT Pub. No.: WO2008/096011
PCT Pub. Date: Aug. 14, 2008

(65) Prior Publication Data
US 2010/0092924 A1  Apr. 15, 2010

(30) Foreign Application Priority Data
Feb. 9, 2007  (EP) .................................... 07425074

(51) Int. Cl.
*C04B 7/02* (2006.01)
(52) U.S. Cl. ........................ 106/35; 106/606; 106/632
(58) Field of Classification Search .................. 523/116; 106/35
See application file for complete search history.

(56) References Cited

U.S. PATENT DOCUMENTS

| | | | | |
|---|---|---|---|---|
| 1,671,104 A * | 5/1928 | Eberly | ............................ | 106/35 |
| 1,791,800 A * | 2/1931 | Colton | ............................ | 106/749 |
| 1,893,696 A * | 1/1933 | Colton | ............................ | 106/749 |
| 1,934,267 A * | 11/1933 | Heyl | ............................ | 516/110 |
| 2,304,391 A * | 12/1942 | Zimmerman | ............................ | 106/638 |
| 2,760,876 A * | 8/1956 | Schulman | ............................ | 106/607 |
| 2,945,769 A * | 7/1960 | Gama et al. | ............................ | 166/292 |
| 3,071,481 A * | 1/1963 | Beach et al. | ............................ | 106/719 |
| 3,278,425 A * | 10/1966 | King et al. | ............................ | 507/109 |
| 3,482,007 A * | 12/1969 | Routh | ............................ | 264/71 |
| 4,081,526 A * | 3/1978 | Asakawa et al. | ............................ | 424/57 |
| 4,337,186 A * | 6/1982 | Crisp et al. | ............................ | 525/362 |
| 4,357,167 A * | 11/1982 | Kellet et al. | ............................ | 106/694 |
| 4,689,080 A * | 8/1987 | Kawahara et al. | ............................ | 106/35 |
| 5,015,256 A * | 5/1991 | Bruce et al. | ............................ | 128/898 |
| 5,415,547 A * | 5/1995 | Torabinejad et al. | ............................ | 433/228.1 |
| 5,769,638 A * | 6/1998 | Torabinejad et al. | ............................ | 433/228.1 |
| 6,458,423 B1 * | 10/2002 | Goodson | ............................ | 427/403 |
| 6,620,232 B1 * | 9/2003 | Kraft et al. | ............................ | 106/404 |
| 6,723,334 B1 * | 4/2004 | McGee et al. | ............................ | 424/423 |
| 6,969,424 B2 * | 11/2005 | Hermansson et al. | ............................ | 106/692 |
| 7,025,824 B2 * | 4/2006 | Axen et al. | ............................ | 106/695 |
| 7,160,949 B2 * | 1/2007 | Ota et al. | ............................ | 525/242 |
| 7,838,573 B2 * | 11/2010 | Primus et al. | ............................ | 523/116 |
| 2002/0009622 A1 * | 1/2002 | Goodson | ............................ | 428/703 |
| 2002/0045678 A1 * | 4/2002 | Lopez et al. | ............................ | 523/116 |
| 2003/0220414 A1 * | 11/2003 | Axen et al. | ............................ | 523/116 |
| 2005/0059757 A1 * | 3/2005 | Bredt et al. | ............................ | 524/3 |
| 2005/0263036 A1 * | 12/2005 | Primus | ............................ | 106/35 |
| 2008/0299093 A1 * | 12/2008 | Yang et al. | ............................ | 424/93.7 |

FOREIGN PATENT DOCUMENTS
EP    1270688 A1 *  1/2003
FR    2661903 A  * 11/1991
(Continued)

*Primary Examiner* — James J Seidleck
*Assistant Examiner* — Peter A Salamon
(74) *Attorney, Agent, or Firm* — Notaro, Michalos & Zaccaria P.C.

(57) ABSTRACT

Compositions containing Montmorillonite and Portland cement for tooth filling are disclosed; such compositions have shown good biocompatibility, excellent marginal adaptation to dentinal walls, short setting time, and improved viscosity.

17 Claims, 5 Drawing Sheets

FOREIGN PATENT DOCUMENTS

| | | | |
|---|---|---|---|
| JP | 59120681 A1 * | 7/1984 |
| JP | 04048980 A * | 2/1992 |
| WO | WO 0236691 A1 * | 5/2002 |
| WO | WO 2005023524 A2 * | 3/2005 |

* cited by examiner

DENTAL CEMENT

TECHNICAL FIELD

The present invention relates to a composition for use in dentistry, a method of producing and uses of such a composition. The present invention further relates to a method of tooth filling by means of the mentioned composition.

BACKGROUND ART

In most dental, in particular endodontic, procedures the achievement of a good seal between the tooth and the filling composition is essential in order to prevent bacterial recontamination of the root canal and ensure long-term clinical success (1, 2). The presence of marginal gaps between the interfaces of retrofilling compositions and root dentin are sites of possible microleakage (3, 4) and penetration of microorganisms and their toxins (5, 6).

Mineral trioxide aggregate (MTA) (ProRoot Dentsply-Maillefer, Baillagues, Switzerland) has been recently introduced for root perforations sealing and as a retrograde filling composition (7,8).

The principal compounds present in MTA are tricalcium silicate, tricalcium aluminate, tricalcium oxide and silicate oxide (7).

Some difficulties are reported by clinicians when using MTA including poor handling characteristic and lengthy setting time. It would be useful to improve those characteristics (9, 10, and 11). Furthermore, a recent study conducted by using a fluid conductive device and by capillary flow porometry reported that root-end fillings performed using MTA presented microleakage (12).

The fluid filtration method was found to be a valid technique to evaluate the sealing ability of root-end filling compositions (13, 14).

DISCLOSURE OF INVENTION

It is an object of the present invention to provide a composition for use in dentistry, a method of producing and uses of such a composition, all of which provide for at least partly eliminating the drawbacks of the prior art, while at the same time being cheap and easy to implement.

According to the present invention, there are provided a composition for use in dentistry, a method of producing and uses of such a composition as claimed in the accompanying independent Claims or in any one of the Claims depending directly or indirectly on the independent Claims.

BRIEF DESCRIPTION OF THE DRAWINGS

A number of non-limiting embodiments of the present invention will be described by way of example with reference to the accompanying figures, in which.

BEST MODE FOR CARRYING OUT THE INVENTION

In accordance with a first aspect of the present invention, there is provided a composition comprising a phyllosilicate.

Phyllosilicates indicate silicates, which naturally occur as sheets (from Greek φύλλον phyllon, leaf). Usually, in nature, phyllosilicates form parallel sheets of silicate tetrahedra with $Si_2O_5$ in a 2:5 ratio.

As far as the present invention is concerned, the phyllosilicates belonging to the Clay mineral group is of particular interest. Advantageously, the phyllosilicate comprises (in particular, consists of) Montmorillonite.

Montmorillonite is a member of the general mineral group the clays. It typically forms microscopic or at least very small platy micaceous crystals. The water content is variable. Some types of Montmorillonite are identifiable by means of ASTM crystallographic tables.

A typical chemical formula of Montmorillonite may be:

$$(Na,Ca)_{0.3}(Al,Mg)_2(Si_4O_{10})(OH)_2 \cdot n(H_2O)$$

The composition of Montmorillonite may be as follows:
Molecular Weight=549.07 gm

| | | | |
|---|---|---|---|
| Sodium | 0.84% Na | 1.13% | $Na_2O$ |
| Calcium | 0.73% Ca | 1.02% | CaO |
| Aluminum | 9.83% Al | 18.57% | $Al_2O_3$ |
| Silicon | 20.46% Si | 43.77% | $SiO_2$ |
| Hydrogen | 4.04% H | 36.09% | $H_2O$ |
| Oxygen | 64.11% O | | |
| | 100.00% | 100.58% | = TOTAL OXIDE |

Empirical Formula: $Na_{0.2}Ca_{0.1}Al_2Si_4O_{10}(OH)_2(H_2O)_{10}$

As far as the present invention is concerned, it is advantageously used a Morillonite having approximately the following formula: $Na_2O \cdot 2MgO \cdot 5Al_2O_3 \cdot 24SiO_2 \cdot (6+n)H_2O$ According to some embodiments, the composition has a weight percentage of phyllosilicate from about 0.4% to about 3.6%, advantageously from about 0.5% to about 3.5%.

In the present text, for "weight percentage" of a component it is intended the percentage of the weight of that component with respect to the entire weight of the composition Advantageously, the composition has a weight percentage of phyllosilicate from about 0.5% to about 2.5%, in particular from about 1% to about 2%.

According to preferred embodiments, the composition comprises a mineral component. Advantageously, the composition has a weight percentage of the mineral component greater than about 50%, advantageously greater than about 60%, advantageously greater than about 70%, advantageously greater than about 75%, advantageously greater than about 80%.

According to some embodiments, the mineral component comprises (preferably, consists of) a mineral silicate-based cement, advantageously Portland cement.

Portland cement is a type of cement in general usage as a hydraulic material. Usually, it is commercialized as a powder produced by grinding Portland cement clinker (more than 90%), a maximum of about 5% gypsum which controls the set time, and up to 5% minor constituents.

According to some embodiments, Portland cement is defined in accordance with the ASTM classification and/or the EN-197.1 classification. These two classifications are not fully coincident.

Advantageously, with reference to the subject matter of the present text, Portland cement is in accordance with EN-197.1; advantageously, Portland cement belongs to class I of EN-197.1.

Advantageously, Portland clinker and Portland cement have the following compositions:

TABLE 1

| Clinker | Mass % | Cement | Mass % |
|---|---|---|---|
| Tricalcium silicate $(CaO)_3 \cdot SiO_2$ | 45-75% | Calcium oxide, CaO | 61-67% |
| Dicalcium silicate $(CaO)_2 \cdot SiO_2$ | 7-32% | Silicon oxide, $SiO_2$ | 19-23% |
| Tricalcium aluminate $(CaO)_3 \cdot Al_2O_3$ | 0-13% | Aluminium oxide, $Al_2O_3$ | 2.5-6% |
| Tetracalcium aluminoferrite $(CaO)_4 \cdot Al_2O_3 \cdot Fe_2O_3$ | 0-18% | Ferric oxide, $Fe_2O_3$ | 0-6% |
| Gypsum $CaSO_4$ | 2-10% | Sulfate | |

According to advantageous embodiments, the Portland cement has substantially the following composition:

TABLE 2

| | |
|---|---|
| $SiO_2$ | 12.24% |
| $TiO_2$ | 0.09% |
| $Al_2O_3$ | 2.11% |
| $Fe_2O_3$ | 0.42% |
| FeO | 0.00% |
| MnO | 0.07% |
| MgO | 1.03% |
| CaO | 67.02% |
| $Na_2O$ | 0.42% |
| $K_2O$ | 0.08% |
| $P_2O_5$ | 0.00% |
| LOI (water) | 16.51% |

Advantageously, the composition comprises $CaSO_4$ and/or $CaCl_2$ and/or $Bi_2O_3$ and/or NaF.

According to some embodiments, the composition has a weight percentage of $SiO_2$ lower than 18%, advantageously, lower than 15%.

According to some embodiments, the composition has a weight percentage of $Fe_2O_3$ lower than 1%.

According to some embodiments, the composition is in powder form, without added water.

Advantageously, the composition as above defined comprises water.

In accordance with a further aspect of the present invention, there is provided a method of producing a composition as above defined, comprising the following steps: grinding the mineral cement silicate-based; heating the mineral cement silicate-based after grinding; and mixing the mineral cement silicate-based with the phyllosilicate so as to obtain a mixture.

Advantageously, the mixture is ground.

According to some embodiments, the heating is carried out at least 400° C. for at least 3 hours, advantageously at about 500° C. for about 4 hours.

Advantageously, the mixture is mixed with water.

In accordance with a further aspect of the present invention, there is provided a composition as above defined for use in dentistry.

In accordance with further aspects of the present invention, the following are provided. A composition as above defined for endodontics. A composition as above defined for tooth filling. A composition as above defined for endodontic filling. A composition as above defined for tooth root-end filling. A composition as above defined for orthograde endodontic filling. A composition as above defined for provisional tooth filling. A composition as above defined for visional luting-prosthetic tooth filling. A composition as above defined for pulp cupping direct and/or indirect. A composition as above defined for apicogenesis and apecification. A composition as above defined for root canal dressing.

For endodontic orthograde filling is usually meant an endodontic filling carried out from the top of the tooth.

For tooth root-end filling is meant a filling carried out in the area of the bottom (apex) of the tooth, usually after an apicectomy. The composition as above defined experimentally demonstrated good properties to induce a fast and complete apicogenesis and apecification (i.e. a good capability of inducing the production of root apical dentin in the area of the tooth apex and the production of a mature and close apex).

For provisional tooth filling is meant a standard tooth filling, for example as carried out after a simple decay has been treated.

For visional luting-prosthetic tooth filling is meant to fix provisional resin crowns and to permanently fix definitive metal-ceramic and full ceramic crown For direct pulp cupping is meant to position the composition in direct contact with an exposed and eventually bleeding pulp so as to induce the production of new tertiary dentin.

For indirect pulp cupping is meant to position the composition in contact with deeper dentin tissue close to the pulp chamber so as to induce the production of tertiary dentin.

For root canal dressing is meant to stop bleeding inside the root canal.

In accordance with a further aspect of the present invention, there is provided the use of a phyllosilicate, for manufacturing a composition as above defined for a use as above defined.

In accordance with a further aspect of the present invention there is provided a method for tooth filling as above defined by means of the above defined composition.

In use, the composition as above defined has shown improved handling characteristics (in particular, flow, fluidity, viscosity) and shorter setting time with respect to MTA.

These advantages over the prior art indicate that the composition as above defined is particularly useful in tooth filling and in the other uses as above defined.

It is also important to point out that the composition as above defined has, surprisingly, experimentally shown the capability of inducing production of tertiary dentin.

Moreover, the above defined composition, in particular where it is in powder form and not previously mixed with water, has shown the surprising capability of solidifying in contact with blood and stop the bleeding of living tissues, such as bone and apical tissues.

Further characteristics of the present invention will result from the description of the following illustrative and non-limiting examples:

Example 1

Formulation

A base cement BCt was prepared mixing and grinding 99% (wt) Portland cement [CEMI® 52,5R(1)] and 1% Calcium Sulphate $CaSO_4$
The obtained powder was treated at 500° C. for 4 hours.
Starting from the BCt several compositions were prepared:
Cement for Root-End Filling
79.5% BCt
14.5% Bismuth Oxide $Bi_2O_3$
5% Calcium Chloride $CaCl_2$
1% Montmorillonite
The components were mixed and grinded.
Cement for Root-End Filling (TC-1%)
84.5% BCt
14.5% Bismuth Oxide $Bi_2O_3$
1% Montmorillonite
The components were mixed and grinded.
Cement for Root-End Filling (TC-2%)
83.5% BCt
14.5% Bismuth Oxide $Bi_2O_3$
2% Montmorillonite
The components were mixed and grinded.
Cement for Endodontic Filling with Antibiotic Activity
84.0% BCt
14.5% Bismuth Oxide $Bi_2O_3$
1% Montmorillonite
0.5% Antibiotic
The components were mixed and grinded.
Cement for Provisional and Definitive Restoration with
Anticaries Activity. Preventive Therapy Cement.
84.2-84.4% BCt
14.5% Bismuth Oxide $Bi_2O_3$
1% Montmorillonite
0.3-0.1% Sodium Fluoride
The components were mixed and grinded.
The grinded components had particles size of about 0.01-0.1 mm.
The above identified powders were mixed with water (for each 2 grams of powder up to 1 mL of water) before use.
The quantity of used water could vary according to the intended use and other features (such as particle dimensions) of the composition/s.
The compositions may also be used in powder form without the addition of water.
All the above defined compositions may be mixed with, instead of water, different water solutions.
Cement for Endodontic Filling with Antibacterial Activity
84.5% BCt
14.5% Bismuth Oxide $Bi_2O_3$
1% Montmorillonite
The components were mixed and grinded, afterwards they were mixed with an aqueous solution (for each 2 grams of powder up to 1 mL of solution) of Chlorexidine (0.5-2.5 by weight in water).
Other Examples of Compositions
84.5% BCt
14.5% Bismuth Oxide $Bi_2O_3$
1% Montmorillonite A)
The components were mixed and grinded, afterwards they were mixed with an aqueous solution (for each 2 grams of powder up to 1 mL of solution) of Articaine (0.4% by weight in water).
(Please Note that Instead of Articaine Other Anaesthetics May be Used)
B)
The components were mixed and grinded, afterwards they were mixed with saline solution (NaCl 0.9% in water) (for each 2 grams of powder up to 1 mL of solution).
C)
The components were mixed and grinded, afterwards they were mixed with aqueous solution of PBS (Phosphate Buffer Solution) (for each 2 grams of powder up to 1 mL of solution).
D)
The components were mixed and grinded, afterwards they were mixed with aqueous solution of DPBS (Dulbecco's Phosphate Buffer Solution) (for each 2 grams of powder up to 1 mL of solution).
E)
The components were mixed and grinded, afterwards they were mixed with aqueous solution of HBBS (Hanks Balanced Buffer Solution) (for each 2 grams of powder up to 1 mL of solution).
F)
The components were mixed and grinded, afterwards they were mixed with FCS (Foetal Calf Serum) for each 2 grams of powder up to 1 mL of FCS).

Example 2 pH Measurement

The cements (TC-1%, TC-2%, white-MTA and Portland cement) were inserted into plastic tubes (1 mm diameter and 10 mm length) using a MacSpadden compactor (Dentsply Maillefer). Five samples were prepared for each composition. Each filled tube was immersed in 10 mL of deionized water and stored at 37° C. in a 100% relative humidity environment. After 4, 24 and 48 h of storage, the tubes were carefully removed and placed into 10 mL of fresh deionized water in order to determine the pH.
The pH of storage water was measured using a pH meter (Phoenix K0201B, Phoenix Electrode Company, Glenmont, Houston, Tex., USA) previously calibrated with standard solutions at pH 4.0 and 7.0 at a temperature of 25° C.

Example 3

Cements Characterization

The composition of white and grey MTA, of Portland cement, of TC-1% and TC-2% was identified using X-ray diffraction (XRD) in an automated powder diffractometer (Philips PW 3719, Philips®, Eindhoven, The Netherlands) using CuKα radiation and a secondary crystal monochromator. Chemical characterization (XRF) was carried out using a quantitative X-ray fluorescence spectrometer (Philips PW 1480, Philips®, The Netherlands). All the samples were analyzed in powder form.

Example 4

Endodontic Sample Preparation

Thirty single-rooted teeth, recently extracted for orthodontic and periodontal reasons were used. All the teeth presented similar length and had not been previously endodontically treated. The crowns were cut at the cementum-enamel junction; the root canals were prepared using a crown-down technique with Gates-Glidden drills (Dentsply Maillefer, Ballaigues, Switzerland) and K-files (Dentsply Maillefer). Instrumentation of the canals was performed with a K-file#30 about 1 mm short of the external apical foramen. This distance was measured by subtracting 1 mm from the length of a K-file#10 just visible at the apex. Copious irrigation with 5 ml NaOCl 5% (Ogna®, Muggiò-Milano, Italy) and 2 ml EDTA 17% (Ogna®) was performed throughout the instrumentation. Finally, the samples were dried with paper points and filled using gutta-percha without sealer and lateral condensation technique. In this way, the gutta-percha could be easily removed after the root-end filling. A horizontal apicectomy was carried out using a cylindrical diamond bur (Intensiv 5424, Grancia Switzerland) mounted on a high-speed handpiece (Castellini Ceramic, Bologna, Italy) under constant water irrigation at a distance of approximately 3 mm from the apex. Successively, a 3.0 mm small round diamond bur (Intensiv 5424, Switzerland) was used to standardize the cavity dimension. The root samples were randomly divided in three groups of 10 samples each. One group was filled using TC-1%, a second group using TC-2% and another group using MTA. Portland cement was not tested for the sealing ability because it is not considered suitable cement for clinical application.

After the root-end filling, the gutta-percha was removed from the root canals using Gates-Glidden drills (Mailleffer) and the external root surface was covered with nail varnish with the exception of the apical 3 mm. During the intervals between the leakage measurements, the teeth were stored in deionized water at 4° C.

Example 5

Fluid Filtration Method

For the sealing ability tests the root samples were prepared as suggested by Fogel et al. (4). They were first fixed by the cementum-enamel junction, using cyanocrylate (ROCKET Heavy DVA, Corona®, CA, USA) to plexiglass supports (2×2×0.5 cm) crossed by an 18 gauge stainless steel tube and then they were connected to a fluid transporter device. Each root specimen was submitted to 6.9 KPa hydraulic pressure for the evaluation of the sealing ability. The measurements of fluid movement were carried out using a fluid conductive system that incorporated a 2.5 gL capacity micro-capillary glass tube (0.7 mm inside diameter) (Microcaps, Fisher Scientific®, GA, USA) positioned between the pressure reservoir and the root segment horizontally positioned. In the micro-capillary glass tube a 0.5 mm air bubble was created. The progress of the air bubble within the micro-capillary glass tube toward the roots was measured over three 5-min periods at 1 minute intervals and the mean calculated. The results were expressed as microliters/minute. The quality of the seal of each specimen was evaluated after 4, 24, 48 h, 1, 2 and 12 weeks from root-filling treatment.

The mean fluid filtration values obtained from the different root-end filling cements were statistically analyzed using a two-way ANOVA test (at a significance level of $p<0.05$). Comparisons between the mean filtration values of the different cements at each given time and between the mean filtration values of the cements at each given time were carried out.

Example 6

Interfacial Micromorphology Evaluation

Five samples were prepared for SEM observations in order to evaluate the presence of marginal gaps between the root-end filling composition and the dentin walls.

A SEM-replica technique was used to observe the interface between the root-end filling compositions and the tooth structure and the presence of gaps between the root end filling composition and the root canal walls. Since the conventional sample preparation for SEM involves dehydration that may induce artifacts in water-containing dental compositions, positive replicas were fabricated from the polyvinylsiloxane impressions using a polyether impression material (Permadyne Garant, 3M/ESPE), according to the replica technique reported by Chersoni et al. (14). The polyether positive replicas were coated with gold and examined using a SEM (JEOL 5400, JEOL, Tokyo, Japan) at 5-10 kV.

Example 7

Results of Examples 1-6

Figure 1:
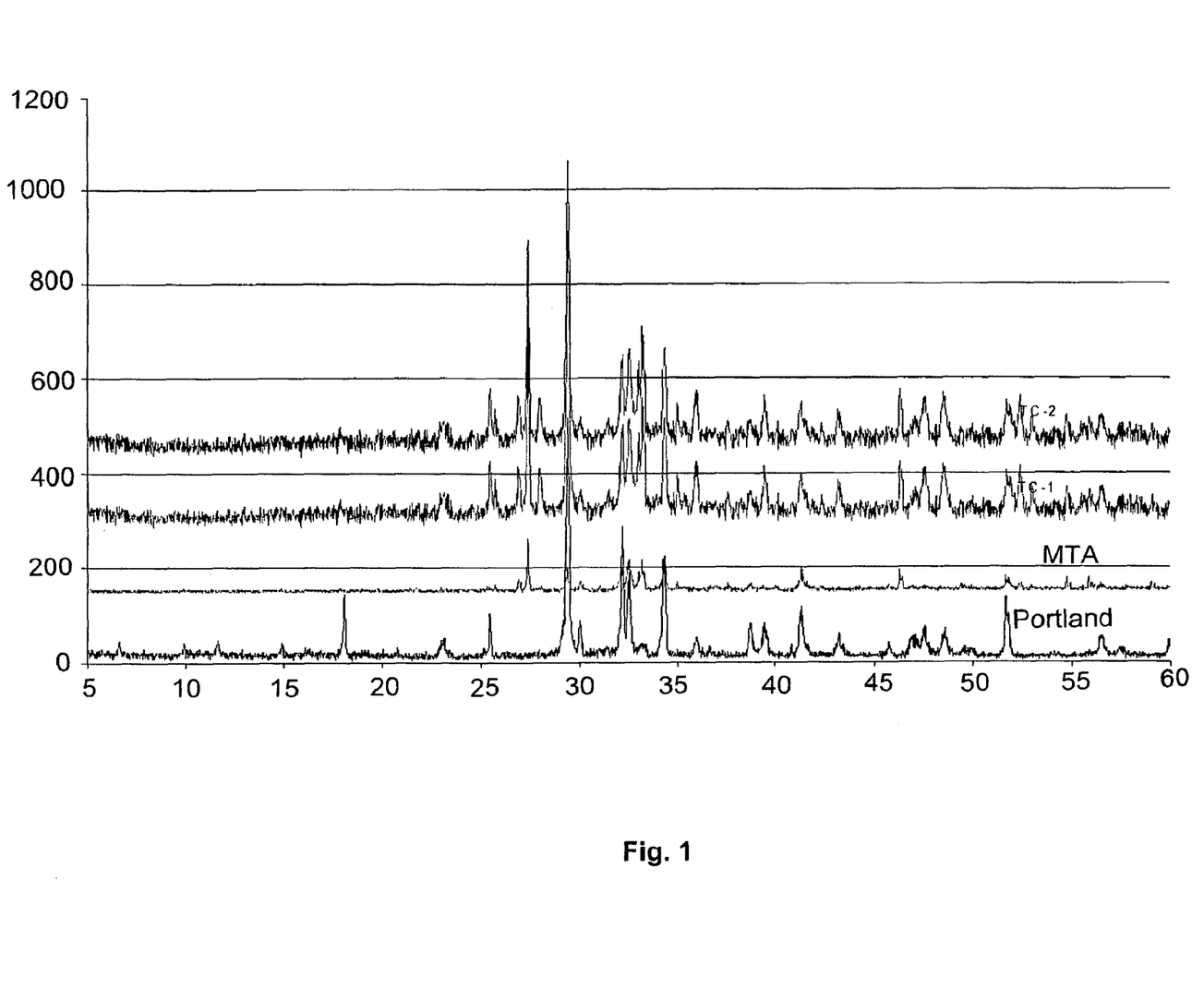
FIG. 1 shows XRD patterns of compositions in accordance with the present inventions [compositions TC-1 (TC-1%) and TC-2 (TC-2%)], and reference material (white-MTA and Portland cement) indicating the presence of the same main constituents; on the y axis counts/seconds are reported; on the x axis 2° Θ is reported.

XRD structural analyses (example 3) of TC-1% and TC-2% showed their complete crystallinity, with definite peaks attributable to specific phases. The same main constituent elements were observed in white-MTA diffractograms (FIG. 1). TC-1%, TC-2%, MTA and Portland cement showed similar patterns. No reflex of phyllosilicate introduced to optimize the products plasticity and workability was detected in the XRD pattern of the experimental cements (TC-1%, TC-2%).

XRF quantitative analyses showed a different composition between both experimental cements, white-MTA and Portland cement. In particular, in the experimental cements lower amounts of $SiO_2$ and $Fe_2O_3$ compounds compared to MTA and Portland cement were found (Table 3).

TABLE 3

| Wt % | TC-1% | TC-2% | white-MTA | PORTLAND CEMENT |
|---|---|---|---|---|
| $SiO_2$ (%) | 13.87 | 13.93 | 27.31 | 18.76 |
| $TiO_2$ (%) | 0.04 | 0.07 | 0.08 | 0.37 |
| $Al_2O_3$ (%) | 2.14 | 2.15 | 2.12 | 5.04 |
| $Fe_2O_3$ (%) | 0.80 | 0.78 | 1.11 | 4.42 |
| FeO (%) | 0.00 | 0.00 | 0.00 | 0.00 |
| MnO (%) | 0.00 | 0.00 | 0.01 | 0.02 |
| MgO (%) | 1.15 | 1.18 | 1.10 | 2.16 |
| CaO (%) | 68.71 | 69.79 | 65.10 | 59.07 |
| $Na_2O$ (%) | 0.51 | 0.55 | 0.37 | 0.27 |
| $K_2O$ (%) | 0.18 | 0.17 | 0.16 | 1.01 |
| $P_2O_5$ (%) | 0.03 | 0.05 | 0.21 | 0.08 |
| LOI (%) | 12.57 | 12.55 | 2.43 | 8.81 |

Table 3 shows the quantitative XRF analysis values for of experimental cements, white MTA and Portland cement groups.

Table 4 shows the pH measurements (example 2) of MTA, Portland cement and experimental cements. TC-1% and TC-2% showed a pH slightly inferior to that of MTA and Portland cement. An evident increase of pH during the first 24 and 48 hours was observed for all the cements, indicating the $OH^-$ release from the compositions.

TABLE 4

| Compositions | pH after 4 h | pH after 24 h | pH after 48 h |
| --- | --- | --- | --- |
| TC-1% | 10.5 | 11.3 | 12.1 |
| TC-2% | 10.5 | 11.2 | 12.2 |
| white-MTA | 11.2 | 12.1 | 12.7 |
| Portland Cement | 12 | 12.8 | 13 |

All cements presented a reduction of the fluid filtration rate over time (example 5) (Table 5). Both experimental cements showed a statistically lower fluid filtration rate than MTA after 4 hours from filling. There were no statistical differences over time between the two experimental cements and MTA at the successive evaluation times.

TABLE 5

|  | TC-1% | TC-2% | white-MTA |
| --- | --- | --- | --- |
| 4 h | $0.8 \pm 0.2^{4-1}$ | $0.8 \pm 0.4^{4-1}$ | $0.9 \pm 0.2^{4-1}$ |
| 24 h | $0.4 \pm 0.3^{4-1}$ | $0.3 \pm 0.3^{4-2}$ | $0.8 \pm 0.5^{B-2}$ |
| 48 h | $0.2 \pm 0.3^{4-2}$ | $0.3 \pm 0.2^{4-2}$ | $0.4 \pm 0.3^{4-2}$ |
| 1 week | $0.1 \pm 0.1^{4-2}$ | $0.1 \pm 0.1^{4-3}$ | $0.1 \pm 0.2^{4-3}$ |
| 2 weeks | $0.0 \pm 0^{4-3}$ | $0.0 \pm 0^{4-4}$ | $0.1 \pm 0.6^{4-3}$ |
| 12 weeks | $0.0 \pm 0^{4-3}$ | $0.0 \pm 0^{4-4}$ | $0.0 \pm 0^{4-4}$ |

Apical fluid filtration values of experimental cements and white-MTA groups at the fixed analysis times after root-filling. The values are expressed as means±standard deviations.

Statistical analyses were carried out among different cement type at the same time (superscript letters A-B) and among different times for a single cement (superscript number 1-4).

Figure 2:
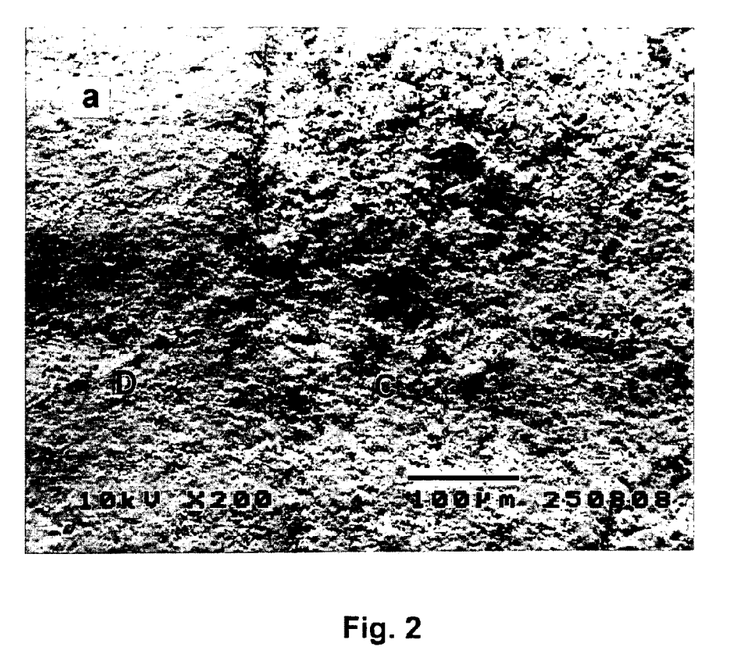
FIG. 2 shows SEM-replica photomicrograph (200×) of a composition in accordance of the present invention, (composition TC-1%) showing a good marginal adaptation at the dentine/cement interface (D=dentine)
Figure 3:
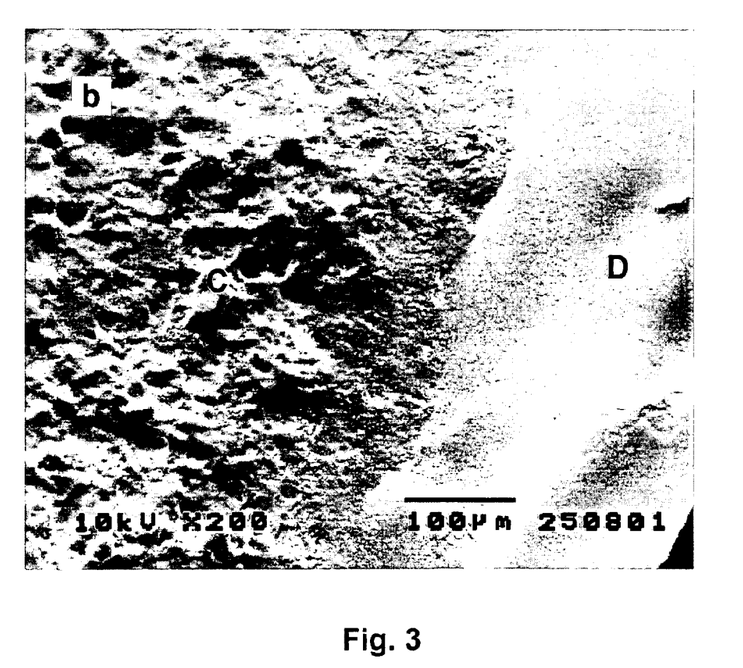
FIG. 3 shows SEM-replica image (200×) of a composition in accordance of the present invention (composition TC-2%) (no gap is visible; a valid and homogeneous interfacial adaptation of the composition (C) to the dentin margins (D) is evident)
Figure 4:
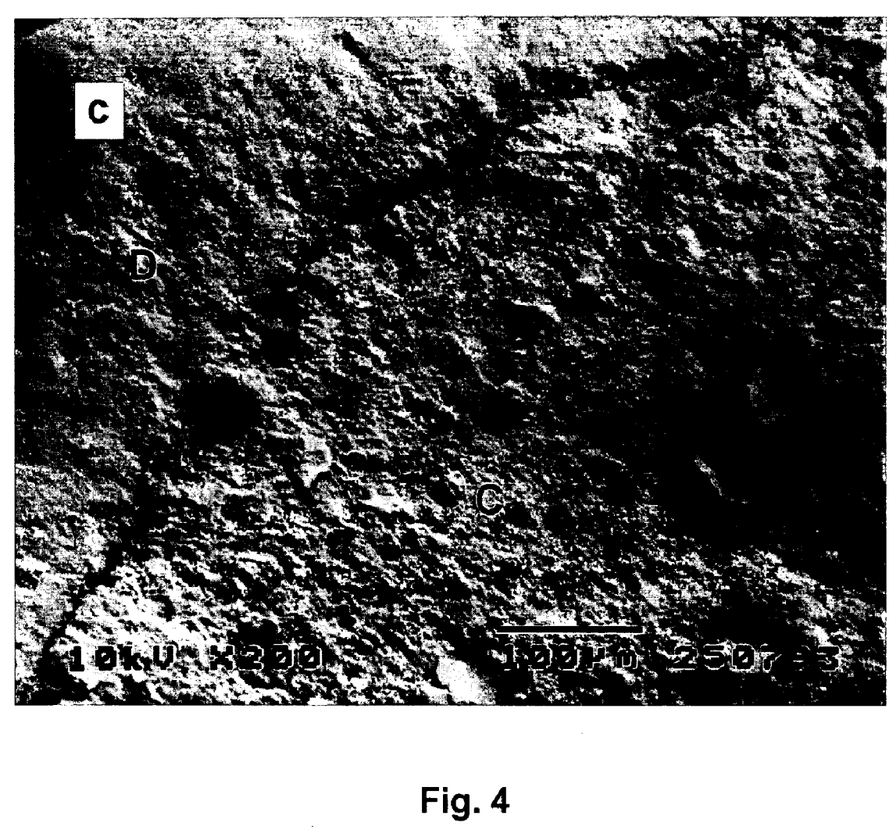
FIG. 4 shows SEM-replica photomicrograph (200×) of the interfacial region between white-MTA (C) and dentinal tissue (D) (a closed gap at the interfacial region is visible)

SEM observations of marginal interfaces between both TC-1% and TC-2% and the root canal walls (example 6) showed a good marginal adaptation to dentinal walls with limited marginal gaps and only sporadic voids along the interface (FIGS. 2 and 3). Specimens treated with MTA indicated the presence of marginal gaps (FIG. 4).

XRD structural analysis results showed that both experimental cements, white and grey MTA and Portland cement were completely crystalline. Furthermore, the experimental cements showed similar patterns to Portland and MTA because their low percentage of the phyllosilicate is not detectable with traditional X-Ray analyses. The XRD analyses of MTA cement is in agreement with previous results reported by Santos et al. (16) and Camilleri et al. (17).

XRF quantitative analysis showed that the experimental cements had constituent elements similar to white-MTA and Portland. Furthermore, it was interesting to highlight the lower amounts of $SiO_2$ and $Fe_2O_3$ compounds in the experimental phyllosilicate-containing cements compared to MTA and Portland cement and the absence, in the experimental cements of other large and chromophore elements.

The pH measurement of TC-1% and TC-2% showed results comparable to those of white-MTA.

The method used in the present study for measuring the fluid filtration of retrograde root filling compositions is a modified version of Pashley's model system for determining fluid transport through dentinal tubules (4, 18). Water transport through existing voids in the obturated canals was measured reproducibly in this way (19). Moreover the fluid filtration system is a non-destructive method, hence the quality of the apical sealing can be observed as function of time.

The results of the sealing ability evaluations showed a similar fluid flow rate for TC-1%, TC-2% and white-MTA. Nevertheless a lower fluid flow rate for both TC-1% and TC-2% after 4 and 24 hours tests was observed. No significant differences were found between the cements at the end of the 12 weeks test.

All cements showed a fluid flow rate reduction over time demonstrating their reliable and stable sealing ability.

The lower fluid filtration observed after 24 hours test in the root samples filled with the TC-1% and TC-2% compared to white-MTA is due to the addition of phyllosilicate to their composition. Probably the phyllosilicate is responsible for high water absorption ability and swelling during water immersion with consequent volume expansion. This characteristic seems to be responsible for an increased adaptation of the cements to the dentinal walls. Hence, the presence of the phyllosilicate seems to increase the water absorption compared to MTA thus reducing the total time of water absorption. TC-1% and TC-2% reached water saturation in a relatively shorter time, while white-MTA uptakes water for a longer time.

The present study demonstrates that both experimental phyllosilicate-containing cements (TC-1%, TC-2%) showed better marginal adaptation than white-MTA, free from gaps and voids. Despite their hydrophilic nature (20) all tested cements showed low porosity of the composition bulk. This feature further decreases the water-pathways and consequently prevent bacterial recontamination and ensure long-term clinical success (1, 2, 21). The addition of the phyllosilicate improved the working properties.

Example 8

Compositions Sterilization

The compositions were sterilized treating them for 1:30 h with antibiotic/antimycotic (10.000 U penicillin, 10 mg streptomycin, 25 µg amphoterycin B/ml $H_2O$), diluted 1:1000 with water; after the samples were washed twice with sterile media and pre-wetted (for 1 h at 37° C.) using culture medium with FBS.

Example 9

Extracts Preparation

The compositions were extracted in D-MEM culture medium for cells according to the International Standard for Biological Testing of Medical devices (1 g/5 mL of medium for 72 h at 37° C.). The control for the composition extracts was provided by D-MEM stored in a polystyrene flask for cell culture.

Example 10

Cell Culture

The human osteosarcoma cell line SaOS-2 (Istituto Zooprofilattico Brescia, Italy) derived from an osteosarcoma was used. SaOS-2 is an immortalized cell line with the phenotipe of mature osteoblasts. SaOS-2 are bone-forming cells and are widely used in bone cell differentiation, proliferation and metabolism studies.

SaOS-2 cells were cultured in D-MEM medium (Dulbecco's Modified Essential Medium-Sigma) supplemented with 10% v/v heat-inactivated fetal bovine serum FBS, 100 units/mL penicillin and 10 µg/mL streptomycin and 2 mM L-Glutamine (acido L-glutammic) in humidified 5% carbon dioxide in 95% air, at 37° C.

For the experiments with solid samples, $1\times10^4$ cells for $cm^2$ were seeded on the cement surface and cultured in complete medium for 3 days (endpoints time at 72 hours); with the extracts, $1\times10^4$ cells for $cm^2$ were seeded in the wells and then the extracts were added (1 mL per well) after 24 h.

After 24 and 72 h (endpoint times), the supernatants were removed entirely from the wells and separately collected and stored at ~20° C. ALP (Alkaline Phosphatase Production) and collagen release were evaluated on supernatant.

Example 11

Cytotoxicity Tests

Testing for cytotoxicity was performed by adding compositions extracts to the SaOS-2 cell culture.

The used extracts consisted of culture medium kept in contact with assayed compositions for 24 and 72 h. For tests, SaOS-2 cells were seeded at a density of 30.000/well and cultured in complete D-MEM medium; after 24 h the medium was removed and replaced with supernatants (extracts of compositions). At fixed endpoints time (24 and 72 h) cultures were tried out for Alamar blue vitality test.

Example 12

Alamar Blue Assay

Viability Test

Alamar blue staining was used for cell viability. The Alamar blue assay measures the products of the redox reactions occurring in mitochondria of viable cells and it is used as index of both viability and metabolic activity of cells (21).

At the fixed endpoint time, the conditioned media was removed and the samples were washed with PBS (Phosphate Buffer Solution). 100 µl of dye (Alamar Blue solution, Biosource International-CA) were added in the wells. And the cells were incubated for 4 h at 37° C. Then the medium was transferred to a 96-well plate in triplicates and the fluorescence was measured using a cytofluorimeter CytoFluor 2350 (Millipore Corporation, Bedford, Mass., USA) with 490 nm excitation wavelength and 530 nm emission wavelength. Cells cultured on plastic were used as control. Results were expressed (as a fraction of the cell activity measured on plastic) as relative fluorescence units (RFU) [Pelliccioni G A, Ciapetti G, Cenni E, Granchi D, Nanni M, Pagani S, Giunti A. Evaluation of osteoblast-like cell response to Proroot MTA (mineral trioxide aggregate) cement. J Mater Sci. Materials in Medicine 2004; 15: 167-73].

Cells osteoblastic-like Saos-2 were seeded on experimental cements (50.000 per $cm^2$) and the test was performed after 72 hours.

Figure 5:
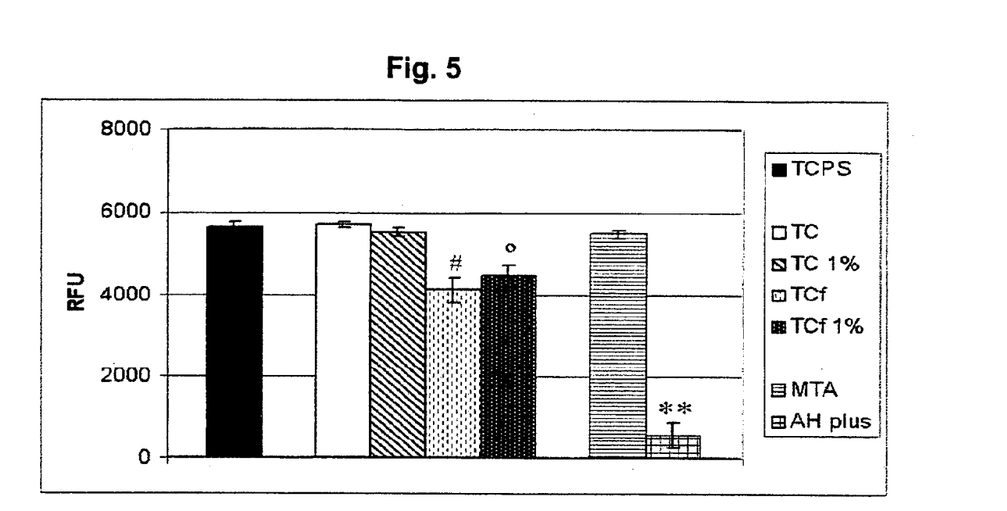
FIG. 5 shows the viability of Saos 2 treated with cements extracts for 72 h: mean±standard error.
Figure 6:
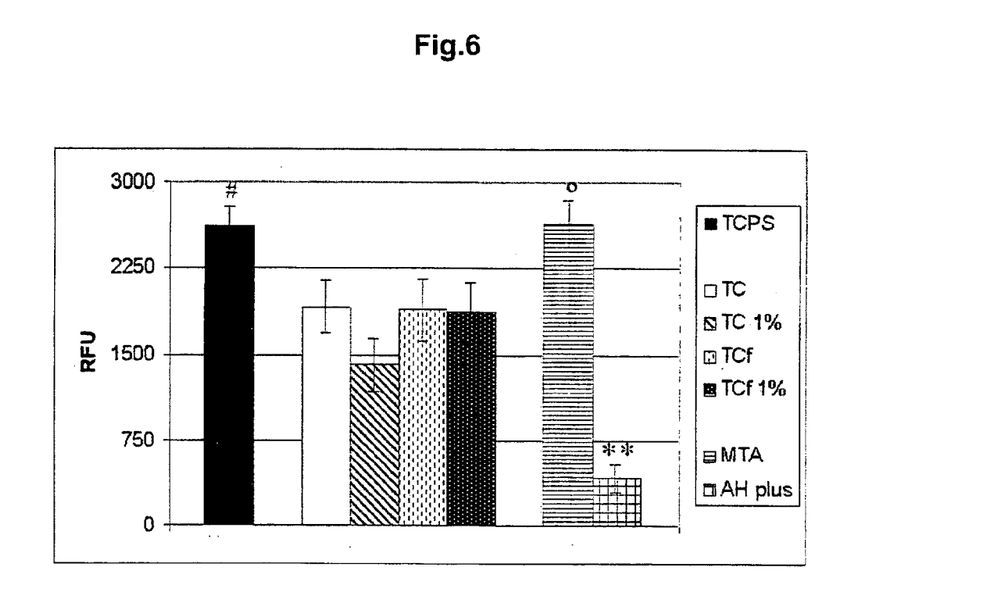
FIG. 6 shows the viability of Saos 2 on solid cements at 72 h: mean±standard error.

Statistical analysis of the results was performed with the StatView™ 5.0.1 software for Windows (SAS Institute Inc., Cary, N.C., USA) and is shown in FIG. 5 [viability of Saos-2 cells treated with cement extracts (example 11)] and 6 [viability of Saos-2 cells on solid cements (example 10)]. The results from viability were reported as mean±standard error and the differences between the samples were analyzed using the Wilcoxon test with a significance level of $p<0.05$.

In FIG. 6:
\*\* $p=0.0051$ AHplus vs all
° $p<0.05$ MTA vs TC, TC 1%, TCf, TCf 1%,
\# $p<0.05$ CTR vs TC, TC 1%, TCf, TCf 1%.

In FIG. 5:
\*\* $p=0.0022$ AHplus vs all
° $p<0.05$ TCf 1% vs all,
\# $p<0.05$ TCf vs all.

In both FIGS. 5 and 6:
AH plus indicates a commercial sealer (epoxy-resin based sealer)
TCPS indicates control plastic for cells cultures
TC 1% indicates TC-1%
TC is a composition differing from TC-1% only in that it does not contain phyllosilicates
TCf 1% indicates a composition which differs from TC 1% only in that it is mixed with a polymer (CEM latex 600 Benfer Chimica, which is a latex aqueous solution) as fluidifying agent instead of water
TCf is a composition differing from TCf 1% only in that it does not contain phyllosilicates.

The results of FIGS. 5 and 6 obtained for TC 1% and TCf 1% show that the compositions are substantially non-toxic and osteoconductive (allows the growth of osteoblasts and thus of bone).

Example 13

Alkaline Phosphatase Activity (ALP)

The metabolic activity of the cells was assayed evaluating the alkaline phosphatase produced and released on supernatants. The ALP assay employed was based on the observation that ALP at alkaline pH catalyses the transformation of colourless p-nitrophenol phosphate to yellow p-nitrophenol. ALP activity was measured following incubation of 100 µl of the cell supernatants with 100 µl of p-nitrophenylphosphate 16 mM solution, (SIGMA diagnostics, 245-10) in glycine buffer for 15 min at 37° C. The production of p-nitrophenol in the presence of ALP was measured by monitoring light absorbance by the solution at 405 nm using a spectrophotometer Spectra III, Tecan. Results are expressed as mmol/L and are shown in FIG. 7.

Figure 7:
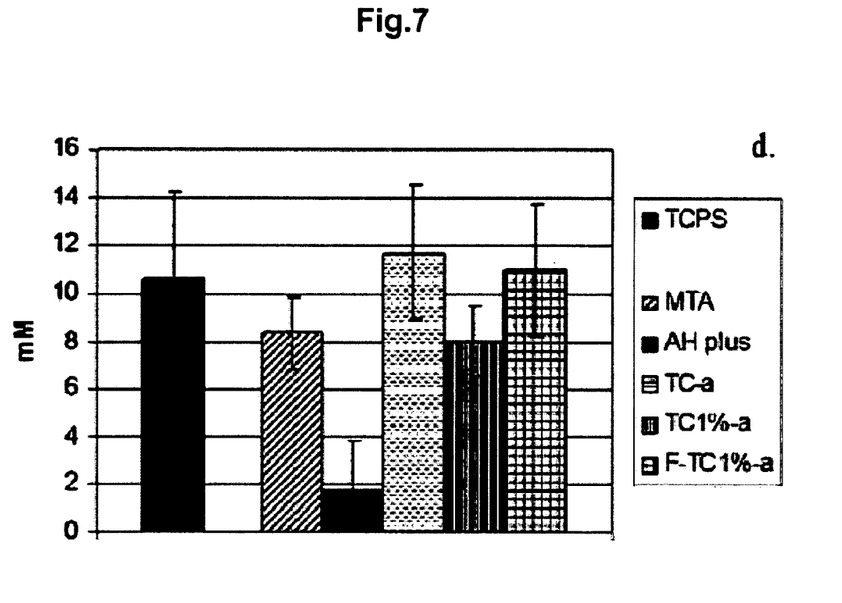
FIG. 7 shows ALP release at 72 h: mean±standard error.

In FIG. 7:
AH plus indicates a commercial sealer (epoxy-resin based sealer)
TCPS indicates control plastic for cells cultures
TC 1%-a indicates composition A of example 1
TC-a is a composition differing from TC 1%-a only in that it does not contain phyllo silicates
F-TC 1%-a is a composition differing from TC 1%-a only in that it has the following starting formulation:
84.3% BCt
14.5% Bismuth Oxide $Bi_2O_3$
1% Montmorillonite
0.2% Sodium Fluoride Enzimatic production is indicative of osteoinductivity (capability of inducing osteoblast growth) and osteoconductivity (capability of allowing osteoblast growth). The results shown in FIG. 7 give evidence that TC 1%-a and F-TC 1%-a are osteoinductive and osteoconductive.

Example 14

SEM Morphological Analysis

Each sample was examined using SEM to observe surface characteristics and cell morphology. FIG. 7 shows SEM images of composition surface morphology after storage in medium culture DMEM (Dulbecco's Modified Eagle's Medium) for 72 hours at 37° C.

TC 1%-a, TC-a, and F-TC 1%-a are as defined in example 13.

Figure 8:
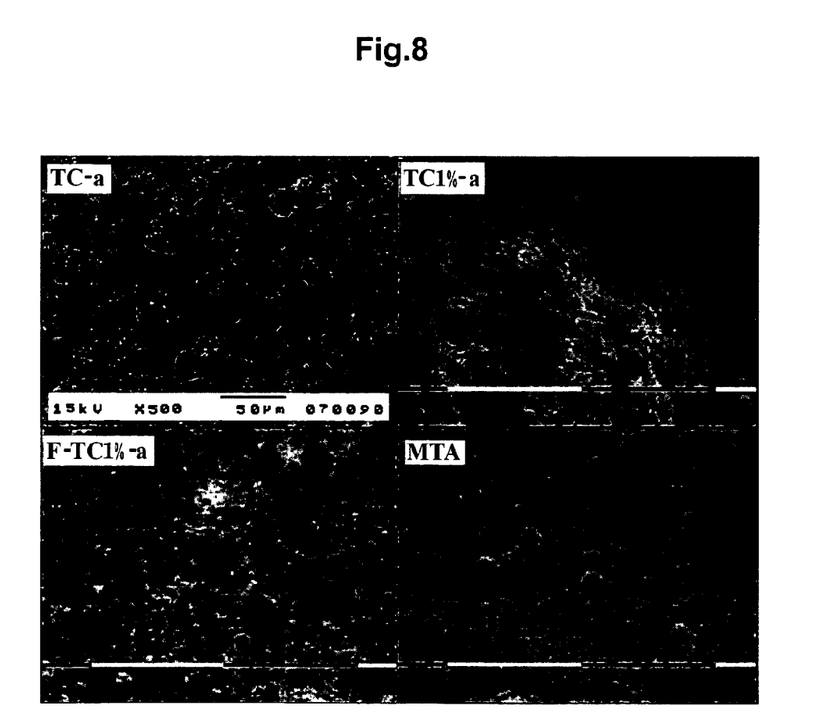
FIG. 8 shows SEM-replica photomicrograph (500×) of cements surfaces.

TC-a shows a coral-like structure and appears uneven and granular with porosities and aggregates of different size (SEM 500×). TC 1%-a appears granular with some porosities (SEM 500×). F-TC 1%-a shows a fairly homogeneous surfaces with many precipitated crystals (SEM 500×). MTA surface shows a coral like structure with thin limited porosity and small voids (SEM 500×).

REFERENCES

1. Khayat A, Lee S, Torabinejad M. Human saliva penetration of coronally unsealed obturated root canals. J Endod 1993; 19: 458-61.
2. Heling I, Gorfil C, Slutzky H, Kopolovic K, Zalkind M, Slutzky-Goldberg I. Endodontic failure caused by inadequate restorative procedures: review and treatment recommendations. J Prosthodontic Dent 2002; 6: 674-8.
3. Spangberg L S W, Acierno T G, Cha B Y. Influence of entrapped air on the accuracy of leakage studies using dye penetration methods. J Endod 1989; 15: 548-51.
4. Fogel H M, Marshall F J, Pashley D H. Effects of distance from the pulp and thickness on the hydraulic conductance of human radicular dentin. J Dent Res 1987; 6: 1381-5.
5. Torabinejad M, Ung B, Kettering J D. In vitro bacterial penetration of coronally unsealed endodontically treated teeth. J Endod; 1990; 16: 566-9.
6. Wu M K, Pehlivan Y, Kontakiotis E G, Wesselink P R. Microleakage along apical root canal fillings and cemented posts. J Prosthet Dent 1998; 79: 264-9
7. Lee S J, Monsef M, Torabinejad M. Sealing ability of a mineral trioxide aggregate for repair of lateral root perforations. J Endod 1993; 19: 541-4.
8. Torabinejad M, Hong C U, McDonald F, Pitt Ford T R. Physical and chemical properties of a new root-end filling material. J Endod. 1995; 21: 349-53.
8. Holland R, de Souza V, Nery M J, Otoboni J A, Bernabe P F E, Dezan E. Reaction of dog's teeth to root canal filling with mineral trioxide aggregate or a glass ionomer sealer. J Endod 1999; 25: 728-30.
9. Abdullah D, Pitt Ford T R, Papaioannou S, Nicholson J, McDonald F. An evaluation of accelerated Portland cement as a restorative material. Biomaterials 2002; 35: 401-10.
10. Maroto M, Barberia E, Planells P, Vera V. Treatment of a non-vital immature incisor with mineral trioxide aggregate (MTA). Dental Traumatol 2003; 19: 165-9.
11. De Bruyne M A, De Bruyne R J, Rosiers L, De Moor R J. Longitudinal study on micro leakage of three root-end filling materials by the fluid transport method and by capillary flow porometry. Int Endod J 2005; 38: 129-36.
12. King K T, Anderson R W, Pashley D H, Pantera E A Jr. Longitudinal evaluation of the seal of endodontic retrofillings. J Endod 1990; 16: 307-10.
13. Yoshimura M, Marshall F J, Tinkle J S. In vitro quantification of the apical sealing ability of retrograde amalgam fillings. J Endod. 1990; 16: 5-12.
14. Chersoni S, Suppa P, Breschi L, Tay F R, Pashley D H, Prati C. Water movement in the hybrid layer after different dentin treatments. Dental Materials 2004; 20: 796-803.
15. Santos D, Moraes J C S, Araujo E B, Yukimitu K, Valerio W V. Physical-chemical properties of MTA and a novel experimental cement. Int Endod J 2005; 38: 443-447.
16. Camilleri J, Montesin F E, Bradyc K, Sweeneyd R, Curtis R V, Pitt Ford T R. The constitution of mineral trioxide aggregate. Dental Materials 2005; 21: 297-303.
17. Cobankara F K, Adanir N, Belli S, Pashley D H. A quantitative evaluation of apical leakage of four root-canal sealers. Int Endod J 2002; 35: 979-984.
18. Pashley D H, Andringa H J, Derkson G D, Derkson M E, Kalathoor S R. Regional variability in the permeability of human dentine. Arch Oral Biol 1987; 32: 519-23.
19. Walker M P, Diliberto A, Lee C. Effect of setting conditions on mineral trioxide aggregate flexural strength. J Endod 2006; 32: 334-336.
20. Wu M K, De Gee A J, Wesselink P R, Moorer W R. Fluid transport and bacterial penetration along root canal fillings. Inter Endod J. 1993; 19: 203-8.

The invention claimed is:

1. Composition for use in dentistry comprising a weight percentage of phyllosilicates from 0.5% to 3.5% and at least 60% of a mineral component, in which the mineral component is Portland cement and the phyllosilicates are Montmorillonite having the following formulation:

$$Na_2O.2MgO.5Al_2O_3.24SiO_2.(6+n)H_2O$$

wherein n is an integer from 1 to 10.

2. Composition according to claim 1, having a weight percentage of Montmorillonite from 0.5 to 2.5%.

3. Composition according to claim 1, having a weight percentage of Montmorillonite from 1 to 2%.

4. Composition according to claim 1, having a weight percentage of Portland cement greater than 70%.

5. Composition according to claim 1, comprising one or more additives selected from the group consisting of: $CaSO_4$, $CaCl_2$, $Bi_2O_3$, NaF.

6. Composition according to claim 1, having a weight percentage of water lower than 13%.

7. Composition according to claim 1, having a weight percentage of $SiO_2$ lower than 18% and a weight percentage of $Fe_2O_3$ lower than 1%.

8. Composition according to claim 1, in powder form.

9. Method for producing a composition according to claim 1, comprising the following steps: grinding the mineral component; heating the mineral component after grinding; mixing the mineral component with the phyllosilicate so as to obtain a mixture.

10. Method according to claim 9, wherein the mixture is ground.

11. Method according to claim 9, wherein the heating is carried out at least 400° C. for at least 3 hours.

12. Composition according to claim 1 for tooth filling.

13. Composition according to claim 1 for tooth root end filling.

14. Composition according to claim 1 for orthograde endodontic filling.

15. Composition according to claim 1 for pulp cupping.

16. Composition according to claim 1 for root canal dressing.

17. Method of tooth filling providing the use of a composition according to claim 1.

* * * * *